United States Patent [19]

Smith

[11] 4,313,237

[45] Feb. 2, 1982

[54] DRIVEN ROTARY TOOTHBRUSH

[76] Inventor: Eric L. Smith, 638 Potomac Ave., Hagerstown, Md. 21740

[21] Appl. No.: 131,371

[22] Filed: Mar. 18, 1980

[51] Int. Cl.$^3$ .......................................... A46B 13/02
[52] U.S. Cl. ....................................................... 15/23
[58] Field of Search ..................................... 15/23, 24

[56] References Cited

U.S. PATENT DOCUMENTS

| 2,044,344 | 6/1936 | Bagnall | 15/23 |
| 2,124,145 | 7/1938 | Merkel, Jr. | 15/23 |
| 2,282,700 | 5/1942 | Bobbroff | 15/22 R |
| 2,435,421 | 3/1948 | Blair | 15/23 |
| 2,562,805 | 7/1951 | Martinez | 15/23 |
| 2,583,886 | 1/1952 | Schlegel | 15/23 |
| 2,628,377 | 2/1953 | Cockriel | 15/23 |
| 2,758,326 | 8/1956 | Keely et al. | 15/23 |
| 3,732,589 | 5/1973 | Burki | 15/22 R |
| 4,048,690 | 9/1977 | Wolfson | 15/22 R |

FOREIGN PATENT DOCUMENTS

| 634607 | 6/1934 | Fed. Rep. of Germany | 15/23 |
| 934142 | 1/1948 | France | 15/23 |
| 1236103 | 6/1960 | France | 15/23 |
| 1299937 | 6/1962 | France | 15/23 |
| 1420912 | 12/1965 | France | 15/23 |
| 666435 | 8/1964 | Italy | 15/23 |

*Primary Examiner*—Edward L. Roberts
*Attorney, Agent, or Firm*—Shanley, O'Neil and Baker

[57] ABSTRACT

An improved driven rotary toothbrush has an electric motor enclosed in a handle and driving a plurality of rotary brushes for simultaneously cleaning multiple tooth surfaces. The rotary brushes are mounted in a brush head adapted to be releasably supported on one end of an elongated brush head support stem having flexible drive shafts extending therealong and having its other end adapted to be releasably mounted on the handle to provide rotary driven connection between the motor and brushes. The releasable mounting of the brush head and of the support stem enables hygenic use of the same motor and handle by a plurality of persons through use of personalized snap-on brush heads and support stems, and also makes possible the easy and economical replacement of the brush heads.

16 Claims, 10 Drawing Figures

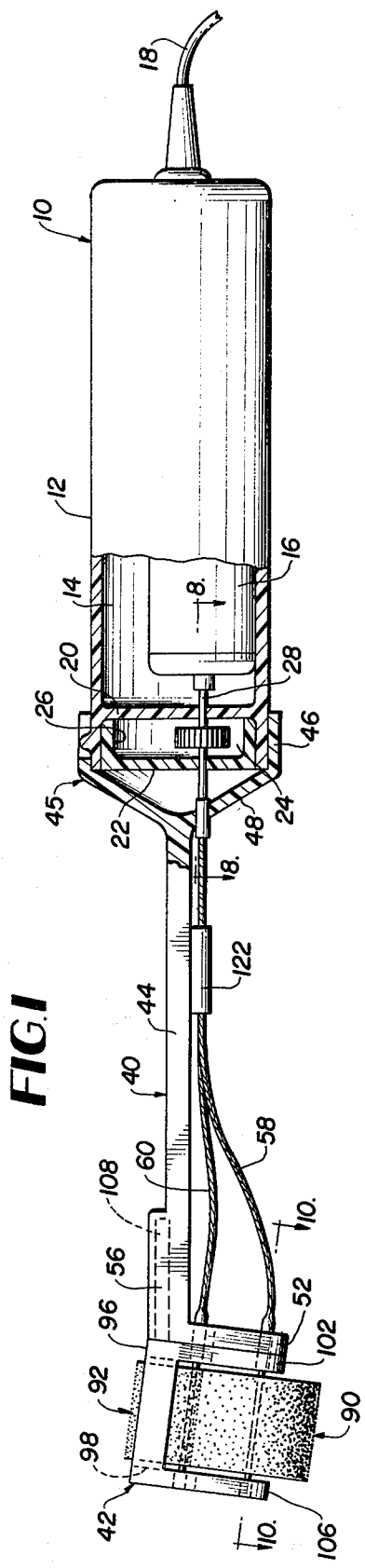
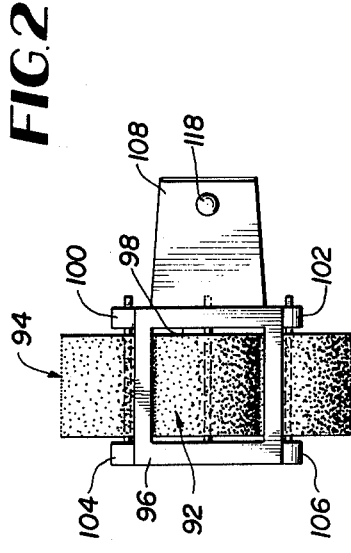
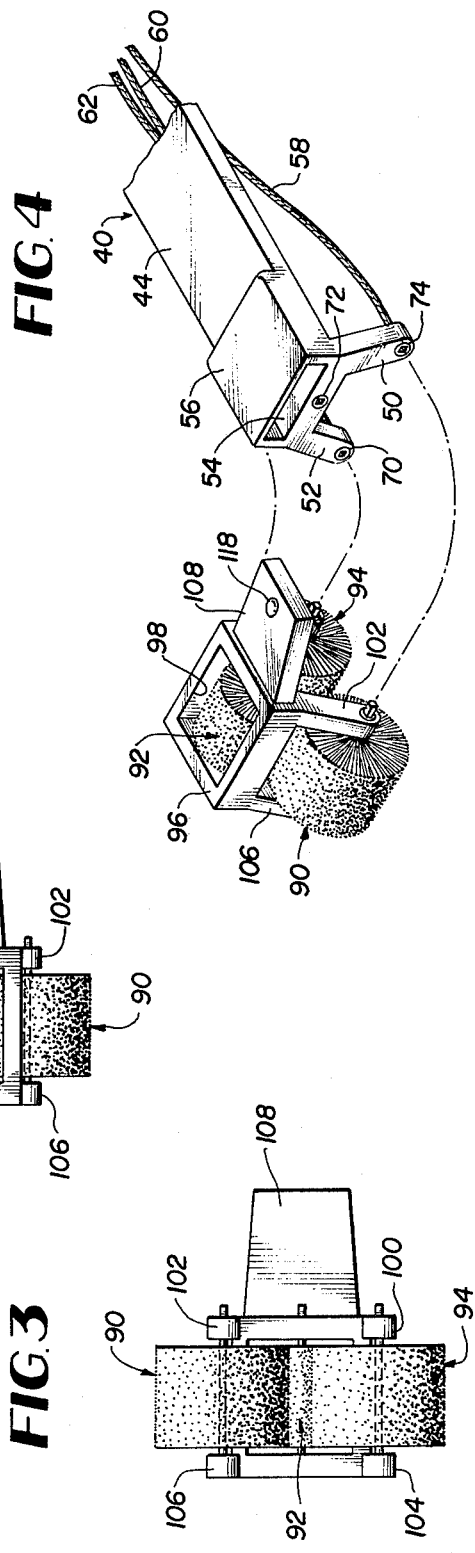

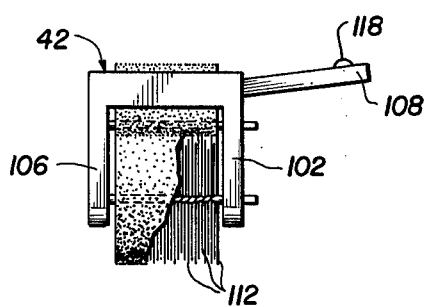
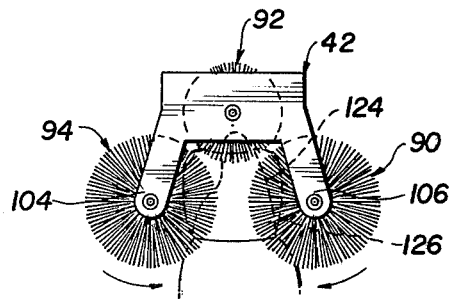
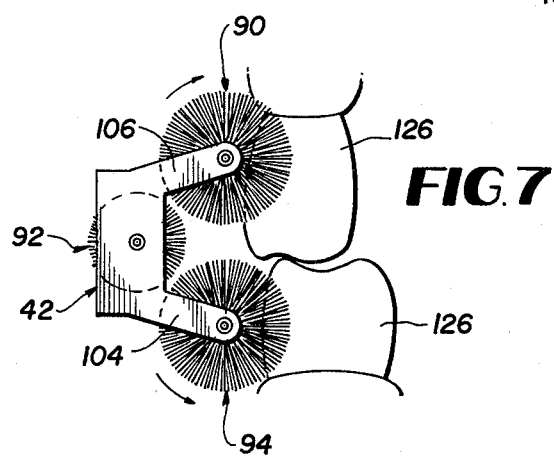
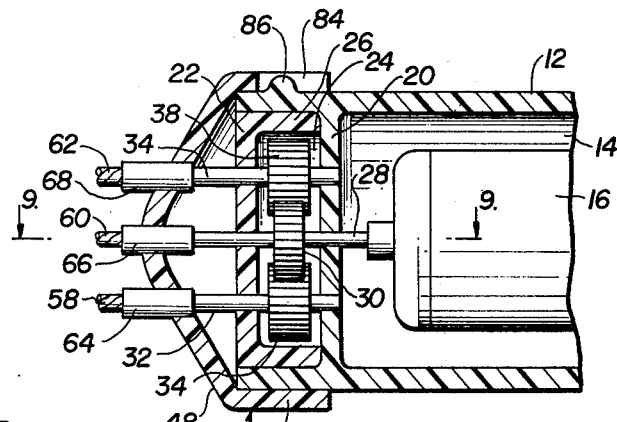

DRIVEN ROTARY TOOTHBRUSH

BACKGROUND OF THE INVENTION

1. Field of the Invention

This invention relates to electrically operated toothbrushes, and more particularly to an improved electrically operated toothbrush having multiple rotary brushes for simultaneously cleaning and massaging multiple tooth and gum surfaces.

2. Description of the Prior Art

Various devices for cleaning and treating the oral cavity have been proposed in which one or more power driven rotary brushes are provided for massaging the gums and cleaning the teeth. Many of these prior art devices have employed a brushing action transversely of the teeth, or generally parallel to the gum line, although it has long been recognized that a brushing action longitudinally of the teeth and away from the gum line is preferred to the exclusive use of a transverse brushing action.

It is also known, for example from U.S. Pat. No. 2,628,377, to provide a driven rotary toothbrush assembly wherein three rotary brushes are mounted for rotation about parallel axes in position to simultaneously engage inner, outer, and bite surfaces of the teeth, with a gear drive arrangement being provided to rotate the brushes engaging the side tooth surfaces in a direction to brush each surface longitudinally of the teeth and away from the gums. However, the toothbrush disclosed in this patent is very bulky and difficult to maneuver in the mouth. Further, the apparatus does not readily lend itself to use by a plurality of persons in that the brushes and brush supports require tools for removal and the brushes are each supported for separate replacement.

SUMMARY OF THE INVENTION

It is a primary object of the present invention to provide an improved driven rotary toothbrush assembly which will rapidly and effectively clean multiple surfaces of teeth in an efficient and hygenic manner.

Another object of the invention is to provide an improved power driven multiple brush rotary toothbrush apparatus which may readily be used by a plurality of persons by the attachment of personal brush heads and support stems.

Another object of the invention is to provide such a multiple brush power driven rotary toothbrush assembly employing a plurality of rotary brushes rotatably supported in a brush head which is releasably mounted on a support stem which, in turn, is readily removably from a sealed handle containing a drive motor.

In the attainment of the foregoing and other objects and advantages of the invention, an important feature resides in providing a rotary drive motor mounted within a sealed housing providing a handle for the toothbrush assembly with the motor support housing having one end adapted to receive and frictionally retain one end of a removable, elongated brush head support system. The rotary motor drives a gear train which, in turn, drives three shafts each having one end projecting through one end wall of the housing to engage and drive suitable coupling means on the ends of three elongated flexible drive shafts mounted on a support stem when the stem is mounted on the end of the motor housing. The flexible shafts have their other ends journaled for rotation in bearings on the distal end of the support stem, and coupling means on the flexible shafts are adapted to cooperate with and drive the rotary brushes supported in a detachable brush head. Cooperating bracket means on the end of the support stem and the brush head mounts the brush head in position to accurately align and engage the coupling means on the flexible shafts with rotary brushes when the brush head is mounted on the stem.

The arrangement just described permits easy snap-on mounting and dismounting of the brush head on the support stem whereby the brushes may be readily changed. At the same time, the snap-on mounting of the support stem enables the apparatus to be used by a plurality of people each utilizing a personal support stem and brush head. The mounting of the brushes in the support head and the arrangement of the gears in the gear train is such that two of the rotary brushes may be used to simultaneously brush the inner and outer surfaces of a person's teeth in a direction longitudinally of the teeth away from the gum while the third brush engages and brushes the end or bite surfaces of the teeth. Preferably the brush head is disposed at a slight angle with respect to the longitudinal axis of the motor housing and drive shaft support stem, and the support stem and brush head are designed to facilitate use of the apparatus without interference from or contact with teeth.

BRIEF DESCRIPTION OF THE DRAWINGS

Other objects and advantages of the invention will become apparent from the detailed description contained hereinbelow, taken in conjunction with the drawings, in which:

FIG. 1 is a side elevation view, partially in section, of a toothbrush according to the present invention;

FIG. 2 is a top plan view of a rotary brush head used on the apparatus shown in FIG. 1;

FIG. 3 is a bottom plan view of the brush head shown in FIG. 2;

FIG. 4 is an exploded perspective view showing the manner of assembling the brush head and support stem of the toothbrush shown in FIG. 1;

FIG. 5 is a side elevation view of the brush head shown in FIGS. 2 and 3;

FIG. 6 is an end view schematically illustrating the apparatus being employed to brush teeth;

FIG. 7 is an end view of the apparatus being employed to simultaneously clean the corresponding surfaces of both upper and lower teeth and illustrating the brushing action away from the gums;

FIG. 8 is an enlarged fragmentary sectional view taken on line 8—8 of FIG. 1;

FIG. 9 is a further enlarged sectional view taken on line 9—9 of FIG. 8; and

FIG. 10 is an enlarged sectional view taken on line 10—10 of FIG. 1.

DESCRIPTION OF THE PREFERRED EMBODIMENTS

Referring now to the drawings in detail, a rotary toothbrush assembly according to the present invention is designated generally by the reference numeral 10 in FIG. 1, and includes an elongated, generally cylindrical molded handle and motor housing 12 having a hollow interior 14 within which is mounted a small electric motor 16. Motor 16 may be battery operated, in which case the batteries would be mounted in the motor cavity 14 of the handle, but preferably an external source of electric current is supplied as through the cord 18 extending out of the rear sealed end of the handle.

A support wall 20 extends transversely of the housing 12, in inwardly spaced relation to the forward end thereof. Wall 20 may be integrally formed with the sidewalls of the housing 12 or, alternatively, may be separately formed as a disc and subsequently rigidly fixed in position within the hollow interior 14 as by bonding. A second transversely extending wall 22 is mounted on and closes the open forward end of housing 12, with wall 22 being rigidly fixed in parallel spaced relation relative to wall 20 to provide a gear chamber 24. If desired, the transversely extending wall 22 can be formed as the end wall of a shallow cylindrical cup, with the sidewalls 26 of the cup acting to accurately align and spaced walls 20 and 22 with respect to one another.

As best seen in FIG. 8, motor 16 has its shaft 28 extending through and journaled in openings in the walls 20, 22, and a small spur gear 30 is mounted on shaft 28 within the gear chamber 24 to be driven by the motor 16. A pair of stub shafts 32, 34 are also journaled in openings in the walls 20, 22 in spaced parallel relation to the motor shaft 28, one on each side thereof as viewed in FIG. 10, and a pair of gears 36, 38 are mounted one on each stub shaft for rotation therewith. Gears 36, 38 mesh with gear 30 so that shafts 32 and 34 are each rotated in a direction opposite to that of shaft 28.

An elongate brush support stem 40 has one end mounted on the forward end of motor housing 12 and is adapted to support a rotary brush head 42 on its other end. The support stem includes an elongated central beam portion 44 having an integrally formed cup-shaped portion 45 on one end for mounting on the motor housing. The cup-shaped portion includes an annular skirt 46 adapted to be telescoped over and frictionally retained on the forward end of the cylindrical housing 12, with a generally cone-shaped transition wall 48 joining the beam 44 and skirt 46. The opposite end of the beam 44 has integrally formed thereon a pair of laterally spaced, downwardly and outwardly diverging legs 50, 52 (see FIG. 4) and a longitudinally extending, generally rectangular slot 54 formed in an enlarged section 56 on its top surface.

Three flexible drive shafts 58, 60 and 62 are rotatably supported on the support stem 40, with the respective flexible shafts each having one end journaled for rotation about a fixed bearing in the conical wall 48. Thus, as shown in FIG. 8, flexible shaft 58 has one end journaled in the wall 48 by a sleeve bearing and coupling assembly 64 described more fully hereinbelow with respect to FIG. 9. Similarly, flexible shaft 60 has one end journaled by sleeve bearing and coupling assembly 66 and flexible shaft 62 is journaled for rotation by sleeve bearing and coupling assembly 68. The forward ends of the respective flexible shafts are also journaled by similar sleeve bearing and coupling assemblies 70, 72 and 74. Thus, shaft 58 is supported in coupling assembly 70 mounted in and extending through the bottom end of leg 52, shaft 60 is supported by assembly 72 mounted in and extending through a downwardly extending flange on the end of the enlarged head 56, and shaft 50 is supported by assembly 74 mounted on and extending through the bottom end of leg 50.

Sleeve bearing and coupling assemblies 64–74 are substantially identical and accordingly only one will be described in detail with reference to FIG. 9, it being understood that the description and reference numerals apply equally to the remaining assemblies. Thus, by way of example, the flexible shaft 60 has its end rigidly retained within a bore in one end of a substantially cylindrical connector member 76. The connector member 76 is journaled for rotation about its longitudinal axis by a bearing sleeve 78 which is rigidly fixed in an opening in the conical end wall 48. The connector 76 has a substantially square, axially extending opening 80 in its other end dimensioned to receive a substantially square end portion 82 on the shaft 28. The opening 80 and square end 82 of the shaft 28 are positioned such that, when the support stem is mounted on the handle, the square end 82 of the shaft 28 will be telescoped into the opening 80 and drive shaft 60. Rotation of the shaft 28 will, of course, also drive all of the flexible shafts through the gear train and the associated couplings described. An axially extending slot 84 formed in the skirt 46 engages a guide 86 on housing 12 as the cup-shaped end of the support stem is mounted on the handle to accurately align the respective couplings with the shaft to be connected thereto.

The brush head assembly 42 is releasably mounted on the distal end of the support stem 40 and includes three rotary brushes 90, 92, 94 supported in driving engagement one with each of the coupling assemblies 70, 72 and 74. The brush head includes a molded A-frame like structure 95 having a generally flat top 96 with an opening 98 formed therein and four integrally formed legs 100, 102, 104, 106 extending downward one from each corner of the top. A substantially flat tongue-like projection 108 is integrally formed on one edge of the top 96 in position to be received within the rectangular recess or slot 54 to releasably mount the brush head on the support stem. The legs on the brush head are arranged so that legs 100, 102 extend in parallel abutting relation to the legs 50, 52, respectively, on the stem.

The rotary brushes 90, 92 and 94 are substantially identical, although preferably the brush 92 is provided with shorter bristles as pointed out below. Each brush comprises an elongated central twisted wire core 110 (see FIG. 10) supporting a plurality of elongated bristles or filaments 112, with the bristles extending radially outward from the wire core to form a substantially cylindrical brush. However, bristles 112 are preferably of various lengths, with the different lengths being intermixed throughout the length of the brushes in order to provide a more uniform and effective brushing action over irregular surfaces of the teeth and gums.

A short cylindrical bearing element 114 is rigidly formed on each end of the twisted wire core 110 in position to be recieved in and supported by aligned pairs of openings in the brush head. Thus brush 90 is supported in openings in legs 100, 102 and brush 94 is supported on the bottom ends of legs 104, 106, while brush 92 is mounted in openings one at each end of the rectangular opening 98 in the flat top portion of the brush head. One end 116 of the twisted wire core 110 of each brush extends outwardly past its bearing 114 and is shaped into a rectangular or square cross section to fit within the correspondingly shaped opening 80 of the coupling member 76 on the forward end of the mating drive shaft.

To manually install the brush head on the support stem, the tongue 108 is inserted into the groove 54 and pushed firmly until the upwardly projecting protuberance 118 on the top surface of the tongue engages a corresponding depression (not shown) in the adjacent surface of the slot 54. In this position, the rearwardly projecting rectangular drive extension 116 on the respective cylindrical brushes will project into and mate with the rectangular opening 80 in the sleeve bearing and coupling assemblies on the forward end of the flexible drive shafts. The tongue 108 and groove 54 as dimensioned so that the brush head is firmly but releasably retained in position, with the protuberance 118 acting to provide a snap-on or detent feature. Further stability for the brush head is provided by the legs 50, 52 extending in abutting relation to the legs 100, 102 and the interfitting connection between the connectors 70 and 74 and the ends of the rotary brushes 90, 94 connected thereto. The support stem 40 can then be mounted on the handle to provide driving engagement between the rearwardly projecting ends of the flexible shaft and the drive motor, thereby providing direct driving connection between the motor and the three rotary brushes. Suitable switch means, not shown, controls operation of the motor.

After using the apparatus, the brushes may be readily cleaned, either with or without removing the brush head from the elongated support stem. Also, the support stem can be removed from the handle if desired to permit another similar support stem and brush assembly to be mounted thereon so that the toothbrush may be used by any number of people, it only being necessary for each user to have a personal support stem and rotary brush head.

The structure of the rotary brush head enables easy access to all teeth in the mouth without interference from the rigid structure of the brush head or of the drive stem. Also, if desired, a stationary, relatively thin-walled flexible tube or housing 120 may be employed to enclose the flexible rotary shafts so that the shafts turn inside the tubular structure. This arrangement may present a more pleasing and hygenic appearance although it is not required for operation of the apparatus. Preferably, the flexible shafts extend through and are supported by a suitable guide 122 at a point intermediate the ends of the beam 44.

As illustrated in FIGS. 6 and 7, the A-frame support structure 95 supports the rotary brushes 90, 92, 94 for rotation about parallel axes in position to provide space therebetween to receive the teeth of a user between the opposed legs of the A-frame. In this position, the brushes 90, 94 simultaneously brush the inner and outer face surfaces of the teeth while the brush 92 engages and brushes the biting surface. Spacing between the brushes 90, 94 and the length of the bristles 112 are such as to enable complete brushing of the surface of either incisors 124 or molars 126 both being illustrated schematically in FIG. 6. Further, by employing bristles of various lengths in each brush, the complete tooth surface will be adequately brushed regardless of surface irregularities. Note, also, that the position of the central brush 92 is such as to enable the brushes 90, 94 to engage and brush or massage the gums at the gum line. Preferably, the bristles of brush 92 are somewhat shorter than those of brushes 90, 94 to thereby provide maximum reach for the brushes 90, 94 onto the gums.

As best seen in FIGS. 1 and 5, the support legs 50, 52 are inclined so that their bottom, or distal ends are spaced slightly farther from the handle than their top ends. This angle of inclination corresponds to the angle of inclination of the support tongue 108 with respect to the top 96 of the brush head so that the support stem is inclined at an acute angle with respect to the rotary axis of the brushes. This angle is preferable within the range of about 8°-15° in order to provide maximum maneuverability of the brush head in the mouth with minimum interference from the support stem and flexible drive shafts. This angle is particularly advantageous when employing the brush to simultaneously brush the corresponding surfaces of both the upper and lower teeth in the manner illustrated in FIG. 7, especially when brushing the inner surfaces of the teeth.

It is also pointed out that the skeletal A-frame structure of the brush head greatly facilitates use of the toothbrush in that only a minimum of rigid structure is required in the mouth. Further, the rigid structure of the brush head is substantially shielded by the projecting bristles of the rotary brushes. In this regard, however, it is pointed out that the relatively straight line angular construction of the brush head in the drawings is for convenience of illustration only and in practice the brush head is constructed to eliminate sharp corners and edges. Similarly, the relatively wide, angular construction of the support stem, and of the releasable support means for mounting the brush head on the support stem are substantially enlarged and schematically illustrated in the drawings for convenience of illustration.

While I have disclosed and described a preferred embodiment of my invention, I wish it understood that I do not intend to be restricted solely thereto, but rather that I do intend to include all embodiments thereof which will be apparent to one skilled in the art and which come within the spirit and scope of my invention.

I claim:

1. An electrically operated rotary toothbrush comprising
   a hollow handle,
   a drive motor sealed in said handle,
   an elongated brush support stem having one end adapted to be releasably mounted on said handle,
   a plurality of elongated drive shafts extending longitudinally of said elongated brush support stem,
   drive means operably connecting said shafts to said motor for rotation thereby when said brush support stem is mounted on said handle, said drive means including
   three shaft members mounted for rotation about spaced axes, and means interconnecting said three shaft members for simultaneous rotation about their respective axes by said motor,
   telescoping stem coupling means for rotatably connecting said elongated shafts one to each of said shaft members while permitting free axial movement therebetween whereby said support stem may be readily mounted upon and removed from said handle,
   friction means for releasably retaining the support stem on said handle,
   guide means adapted to align said elongated shafts with said shaft members when the support stem is mounted on the handle,
   a brush head including a plurality of rotary brushes mounted for rotation about spaced generally parallel axes,
   mounting means for releasably supporting said brush head on the other end of said support stem, said mounting means including cooperating means on said stem and said brush head for frictionally retaining the brush head on the stem, and
   brush coupling means rotatably coupling said rotary brushes one to each of said plurality of elongated drive shafts when the brush head is mounted on said support stem.

2. The toothbrush as defined in claim 1 wherein said brush coupling means comprises cooperating telescoping means on each of said brushes and on each of said elongated drive shafts and adapted to cooperate with one another to permit free axial movement between the elongated drive shafts and the brushes connected thereto whereby the brush head can be readily mounted on and removed from said support stem.

3. The toothbrush as defined in claim 2 wherein said mounting means on said brush head and said support stem comprises detent means for releasably retaining the brush head on the support stem.

4. The toothbrush as defined in claim 3 wherein said mounting means comprises an elongated tongue integrally formed on one of said brush head or said support stem and a slot formed on the other of said brush head or support stem, said slot being adapted to receive and support said tongue.

5. The toothbrush as defined in claim 4 wherein the axes of rotation of said brushes extend at an acute angle relative to the longitudinal axis of the elongated support stem, the acute angle being divergent in the direction from the brushes to the handle.

6. The toothbrush as defined in claim 1 wherein said cooperating means on said brush head and said support stem comprises detent means for releasably retaining the brush head on the support stem.

7. The toothbrush as defined in claim 6 wherein said cooperating means comprises an elongated tongue integrally formed on one of said brush head or said support stem and a slot formed on the other of said brush head or support stem, said slot being adapted to receive and support said tongue.

8. The toothbrush as defined in claim 7 wherein the axes of rotation of said brushes extend at an acute angle relative to the longitudinal axis of the elongated support stem, the acute angle being divergent in the direction from the brushes to the handle.

9. The toothbrush as defined in claim 1 wherein said plurality of elongated drive shafts comprise three flexible drive shafts extending longitudinally of said support stem, and wherein said brush head supports three elongated, generally cylindrical rotary brushes in position to be releasably coupled one to each of said flexible drive shafts.

10. The toothbrush as defined in claim 1 wherein said brush head comprises an integrally formed, generally A-frame shaped frame member including a generally rectangular body having a generally rectangular opening extending therethrough and four legs extending from each corner thereof and wherein two of said brushes are mounted on the ends of said legs spaced from said body and the third said brush is mounted for rotation in said generally rectangular opening.

11. The toothbrush as defined in claim 10 wherein said brushes mounted on said legs are driven for rotation in opposite directions to brush opposed surfaces of a person's teeth simultaneously and in a direction away from the gums.

12. The toothbrush as defined in claim 10 wherein each of said brushes comprises an elongated twisted wire support engaging and supporting a plurality of generally radially extending bristles, said bristles being of various lengths and the various lengths being randomly dispersed along the length of the brush.

13. An electrically operated rotary toothbrush comprising
a hollow handle,
a drive motor sealed in said handle,
an elongated brush support stem having one end adapted to be releasably mounted on said handle,
three elongated flexible drive shafts extending longitudinally of said elongated brush support stem,
drive means operably connecting said shafts to said motor for rotation thereby when said brush support stem is mounted on said handle,
a brush head including three elongated, generally cylindrical brushes mounted for rotation about spaced parallel axes in position to be releasably coupled one to each of said flexible drive shaft,
mounting means for releasably supporting said brush head on the other end of said support stem, said mounting means including an elongated tongue and a cooperating slot formed one on each of said stem and said brush head for frictionally retaining the brush head on the stem, a detent means releasably retaining the brush head on the support stem, said brush head being mounted so that the axes of rotation of said brushes extend at an acute angle relative to the longitudinal axis of said support stem, and
coupling means rotatably coupling said rotary brushes one to each of said plurality of elongated drive shafts when the brush head is mounted on said support stem.

14. The toothbrush as defined in claim 13 further comprising drive means in said handle including three shaft members mounted for rotation about spaced parallel axes and gear means interconnecting said three shaft members for simultaneous rotation, one of said shaft members being driven by said motor.

15. The toothbrush as defined in claim 14 further comprising telescoping coupling means for rotatably connecting said flexible shafts one to each of said shaft members while permitting free axial movement therebetween whereby said support stem may be readily mounted upon and removed from said handle, and friction means for releasably retaining the support stem on said handle.

16. The toothbrush as defined in claim 15 further comprising guide means on said support stem and said handle for aligning said flexible shafts with said shaft members when the support stem is mounted on the handle.

* * * * *